(12) United States Patent
Chen et al.

(10) Patent No.: US 9,872,946 B2
(45) Date of Patent: Jan. 23, 2018

(54) TEMPERATURE-ADJUSTED HEATER FOR TRANSFUSION

(71) Applicant: Shurcon Manufacturing (Zhejiang) Co., Ltd., Jiaxing (CN)

(72) Inventors: Sherry Chen, Jiaxing (CN); Qi Bao, Jiaxing (CN)

(73) Assignee: SHURCON MANUFACTURING (ZHEJIANG) CO., LTD., Jiaxing (CN)

(*) Notice: Subject to any disclaimer, the term of this patent is extended or adjusted under 35 U.S.C. 154(b) by 134 days.

(21) Appl. No.: 14/944,351

(22) Filed: Nov. 18, 2015

(65) Prior Publication Data

US 2016/0136340 A1   May 19, 2016

(30) Foreign Application Priority Data

Nov. 19, 2014   (CN) .......................... 2014 1 0660814

(51) Int. Cl.
  *H05B 1/02*   (2006.01)
  *A61M 1/02*   (2006.01)
  *A61M 5/14*   (2006.01)

(52) U.S. Cl.
  CPC ............. *A61M 1/0281* (2013.01); *A61M 5/14* (2013.01); *A61M 2205/3653* (2013.01)

(58) Field of Classification Search
  CPC ................. A61M 1/0281; A61M 5/14; A61M 2205/3653; H05B 1/025; H05B 3/0085; H05B 2203/021
  USPC .......................... 219/535, 494, 497, 491, 533
  See application file for complete search history.

(56) References Cited

U.S. PATENT DOCUMENTS

| | | | | |
|---|---|---|---|---|
| 3,668,597 A * | 6/1972 | Nomura | ................. | H01C 10/50 338/198 |
| 4,167,663 A * | 9/1979 | Granzow, Jr. | ........... | A61M 5/44 219/494 |
| 4,532,414 A * | 7/1985 | Shah | ...................... | A61M 5/44 165/46 |
| 4,707,587 A * | 11/1987 | Greenblatt | .............. | A61M 5/44 165/102 |
| 4,709,135 A * | 11/1987 | Dietrich | .................. | A61M 5/44 392/470 |
| 4,906,816 A * | 3/1990 | van Leerdam | .......... | A61M 5/44 392/470 |
| 5,195,976 A * | 3/1993 | Swenson | ........... | A61M 5/16886 604/113 |
| 6,236,809 B1 * | 5/2001 | Cassidy | .................. | A61M 5/44 392/465 |
| 7,153,286 B2 * | 12/2006 | Busby | ..................... | A61M 1/28 210/252 |

(Continued)

*Primary Examiner* — Mark Paschall
(74) *Attorney, Agent, or Firm* — Hemisphere Law, PLLC (57) ABSTRACT

A temperature-adjusted heater for transfusion includes a clamping member and a temperature-controlled unit. The clamping member defines a through hole, for a transfusion tube pass through and fixed therein. The temperature-controlled unit connecting to power supply, includes a heating member, an adjusting current circuit, and an adjusting button. The heating member is mounted in the clamping member, in communication with the through hole, and firmly against the transfusion tube. The heating member and the adjusting button are in series with the adjusting current circuit, and the adjusting button is operated to change the resistance value of the adjusting current circuit.

6 Claims, 9 Drawing Sheets

(56) References Cited

U.S. PATENT DOCUMENTS 7,988,665 B2 * 8/2011 Ogawa .................... A61M 5/44
604/113

* cited by examiner

TEMPERATURE-ADJUSTED HEATER FOR TRANSFUSION

CROSS-REFERENCES TO RELATED APPLICATIONS

This application claims the priority of Chinese patent application number201410660814.8, filed on Nov. 19, 2014, the entire contents of which are incorporated herein by reference.

FIELD OF THE INVENTION

The present invention generally relates to supplementary means for transfusion and, more particularly, to the temperature-adjusted heater for transfusion.

BACKGROUND

When a patient is on a drip, the perfusion liquid directly flows into the patient from an infusion bottle, to treat the disease. The cold perfusion liquid may cause the patients cold, painful, even having a crick. At present, during dripping, a hot water bottle or a hot-water bag applied to heat the perfusion tub many also help to ease the pain.

However, the hot water bottle is extremely difficult controlled to maintain a proper temperature. What is more, the hot water is easy to hurt person because of careless. In additionally, the temperature of the hot water can't keep hot, so that hot water in the hot water bottle or the hot-water bag must be changed after a while. Therefore, hot water bottle or the hot-water bag applied to heat the perfusion tub is inconvenient and tedious.

The disclosed methods and systems are directed to solve one or more problems set forth above and other problems.

BRIEF SUMMARY OF THE DISCLOSURE

The present disclosure includes temperature-adjusted heater for transfusion. The temperature-adjusted heater for transfusion includes a clamping member and a temperature-controlled unit. The clamping member defines a through hole, for a transfusion tube pass through and fixed therein. The temperature-controlled unit connecting to power supply, includes a heating member, an adjusting current circuit, and an adjusting button. The heating member is mounted in the clamping member, in communication with the through hole, and firmly against the transfusion tube. The heating member and the adjusting button are in series with the adjusting current circuit, and the adjusting button is operated to change the resistance value of the adjusting current circuit.

Other aspects of the present disclosure can be understood by those skilled in the art in light of the description, the claims, and the drawings of the present disclosure.

DETAILED DESCRIPTION

Reference will now be made in detail to exemplary embodiments of the invention, which are illustrated in the accompanying drawings. Wherever possible, the same reference numbers will be used throughout the drawings to refer to the same or like parts.

Figure 1:
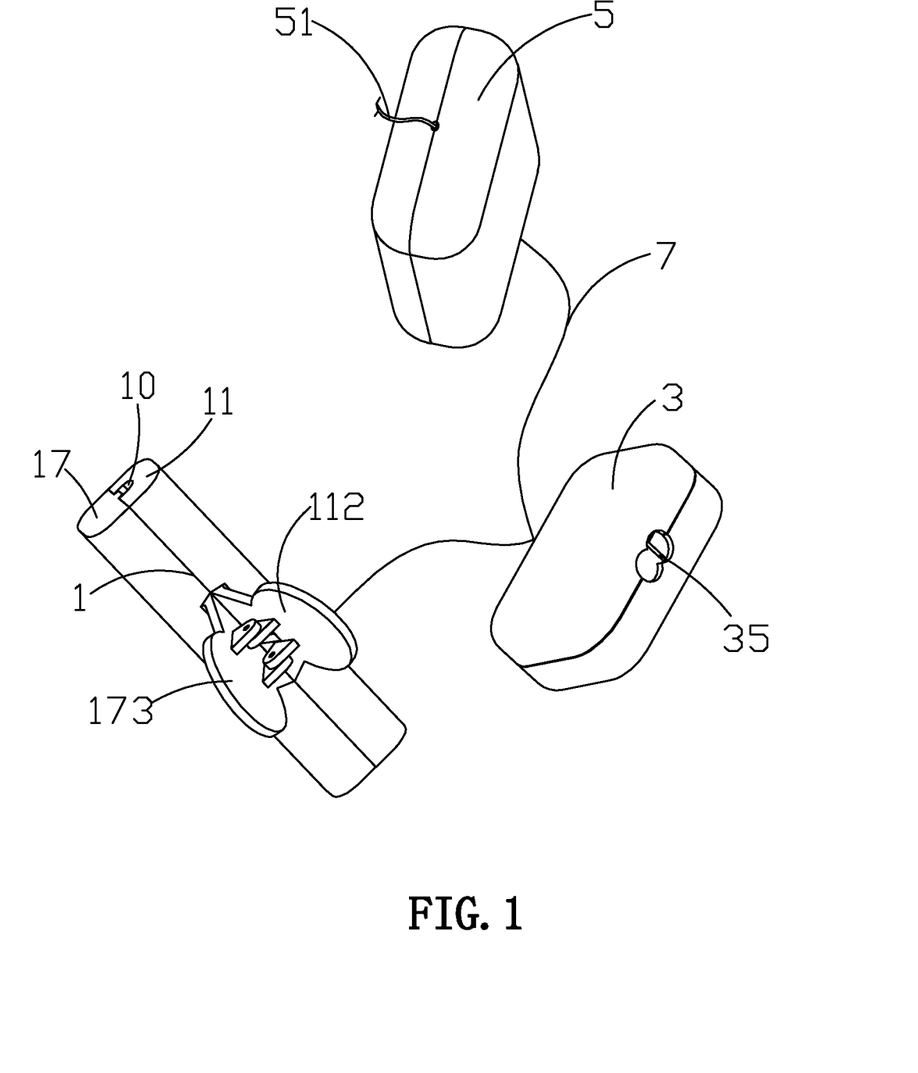
FIG. 1 is an exploded view of the temperature-adjusted heater for transfusion, the temperature-adjusted heater for transfusion comprising a clamping member, a temperature-controlled unit, and a power adapter.
Figure 8:
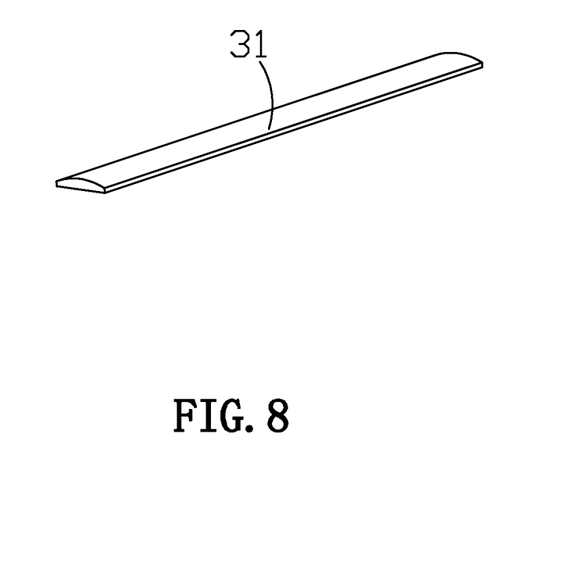
FIG. 8 is an enlarged view of a heating member of the temperature-controlled unit.
Figure 9:
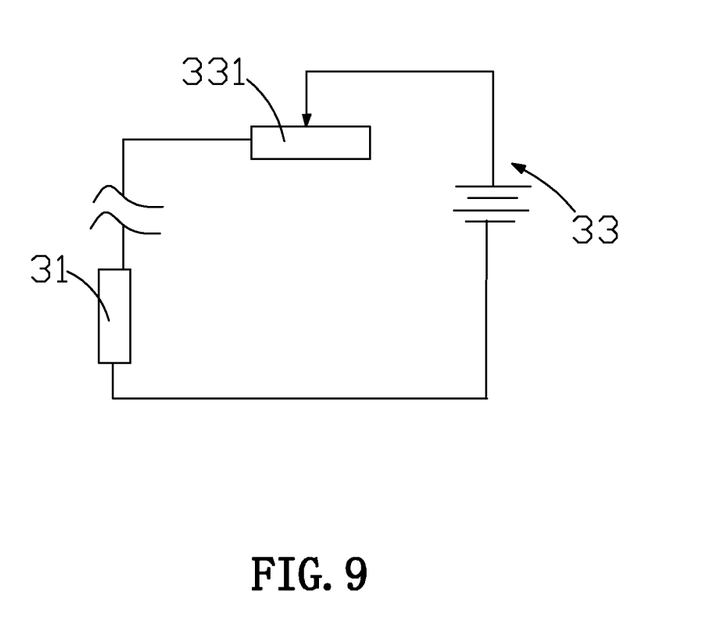
FIG. 9 is an adjusting current circuit of the temperature-controlled unit in accordance with an embodiment.

Referring to FIGS. 1, 8, and 9, the invention of a temperature-adjusted heater for transfusion includes a clamping member 1, a temperature-controlled unit 3, a power adapter 5, and a plurality of power wires 7 connecting the temperature-controlled unit 3 and the power adapter 5. The clamping member 1 is used for clamping a perfusion tube or a blood transfusion tube, so that the temperature-controlled unit 3 conveniently heats the blood or the transfusion liquid. The temperature-adjusted heater for transfusion is used in blood transfusion similar to use in perfusion. So, in the following description, the temperature-adjusted heater for transfusion is used in perfusion as example. Specifically, the clamping member 1 defines a through hole 10, for the perfusion tube pass through and fixed therein. The temperature-controlled unit 3 includes a heating member 31, an adjusting current circuit 33, and an adjusting button 35. The heating member 31 is installed in the clamping member 1, and firmly touched to the perfusion tube, for heating the transfusion liquid. The heating member 31 and the adjusting button 35 electrically connect to the adjusting current circuit 33, respectively. The power adapter 5 electrically connects to the temperature-controlled unit 3, and the power adapter 5 includes a power cord 51 connection with a power supply. The power adapter 5, the heating member 31, the adjusting current circuit 33, the adjusting button 35 and the power supply are electrically connected in series via the power wires 7.

When put on a drip for a patient, the power cord 51 is connected to the power supply to provide power for the temperature-controlled unit 3. Then, the adjusting current circuit 33 switches on, so that current flows through the heating member 31. Therefore, the heating member 31 becomes hot, that heats the perfusion tube and heating the transfusion liquid. According to the requirement of the patient, the hot value can be adjusted via slid the adjusting button 35.

In this invention, referring to FIGS. 1 to 7, the clamping member 1 includes a first holding body 11 and a second holding body 17. The first holding body 11 pivotably mounts to the second holding body 17, and can be rotated to move towards to or away from each other.

Figure 4:
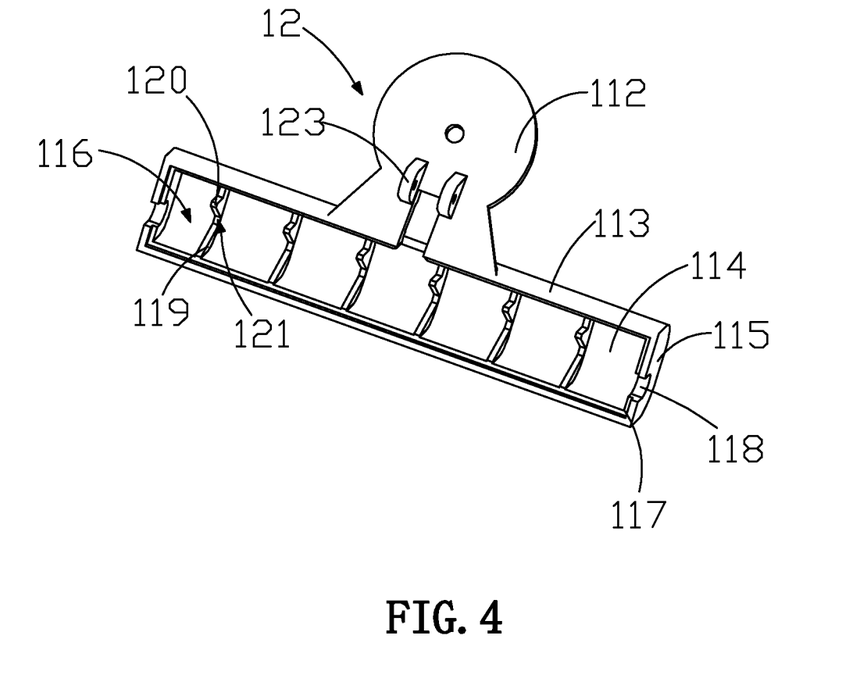
FIG. 4 is an enlarged view of the first holding body of FIG. 3.

The first holding body 11 includes a mounting base 12, a securing plate 13, a cover plate 15, and a plurality of supporting panels 119. The mounting base 12 is similar to a case without a cover. Specifically, the mounting base 12 includes a side panel 114, two fixing panels 113 extending from opposites sides of the side panel 114, and two end panels 115. Each end panel 115 connects to a corresponding end of each fixing panel 113. The side panel 114, the fixing panels 113 and the ends panel 115 cooperatively define an accommodating space 116. An inner sidewall of the fixing panels 113 and the ends panel 115 extend a supporting block 117, used for positioning the securing plate 13. The side panel 114 defines a fixing hole (not show), for two power wires 7 pass through to connect to ends of the heating member 31.

A first operation knob 112 extends from one of the fixing panels 113. In the other embodiment, the fixing panels 113 can be omitted, and the side panel 114 is substantially arcuate, so that, the first operation knob 112 extends from a circumference portion of the side panel 114.

Each end panel 115 defines a fixing groove 118, and each fixing groove 118 extends through a free end thereof, away from the side panel 114. The fixing grooves 118 are aligned with each other.

The supporting panels 119 are accommodated in the accommodating space 116. Two ends of each supporting panel 19 connect to the corresponding fixing panels 113, respectively. Each supporting panel 19 defines a receiving groove 121. A wedge-shaped block 120 extends from each supporting panel 19, adjacent with the corresponding receiving groove 121.

Figure 5:
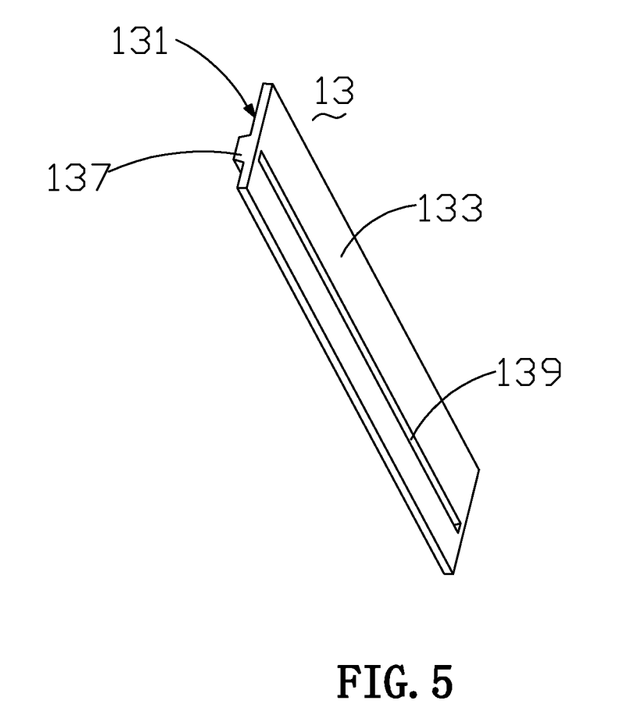
FIG. 5 is an enlarged view of the securing member of FIG. 3.

Referring to FIG. 5, length of the securing plate 13 is shorter than the side panel 114. The securing plate 13 includes a first side 131 and a second side 133 opposite to the first side 131. The first side 131 defines a plurality of clipping holes (not shown), engaged with the wedge-shaped blocks 120, correspondingly. A rib 137 protrudes from the first side 131, and extends transversely through opposite ends of the securing plate 13. The second side 33 defines a mounting groove 139, opposite to the rib 137. The mounting groove 139 also extends transversely through the opposite ends of the securing plate 13.

Figure 6:
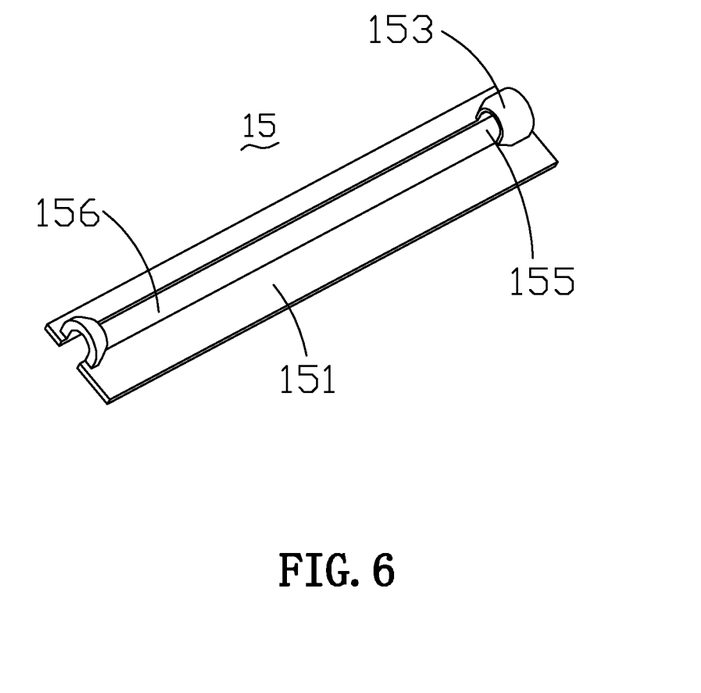
FIG. 6 is an enlarged view of the cover plate of FIG. 3.

Referring to FIG. 6, the cover plate 15 includes a plate 151, and two connecting blocks 153 connecting to opposite ends of the plate 151, respectively. The plate 151 defines a through groove 156 extending through the opposite ends thereof. Each connecting block 153 defines a flute 155, in communication with the through groove 156. In other words, the through groove 156 divides the plate 151 into two sub-plates, and the connecting blocks 153 connect the sub-plates together.

When assembling the first holding body 11, the securing plate 13 is mounted to the supporting block 117, with the first side 131 of the securing plate 13 firmly fixed to the mounting base 12. Go in detail, the wedge-shaped blocks 120 are engaged in the clipping holes of the first side 131, and meanwhile, the rib 137 is locked in the receiving grooves 121. Then, the heating member 31 is mounted in the mounting groove 139. After then, the cover plate 15 is installed to the mounting base 12, with plate 151 pressed against the second side 133 of the securing plate 13. Moreover, the connecting blocks 153 are received in the accommodating space 116, and against the corresponding ends panel 115, respectively. In this moment, the flutes 155 are aligned with the fixing groove 118. The through groove 156 is aligned with the mounting groove 139, both communicating with the through hole 10, so that, the heating member 31 is outside the through hole 10, to heat the blood or the transfusion liquid. Furthermore, the plate 151 is secured to the mounting base 12 via fasteners, such as screws.

Figure 7:
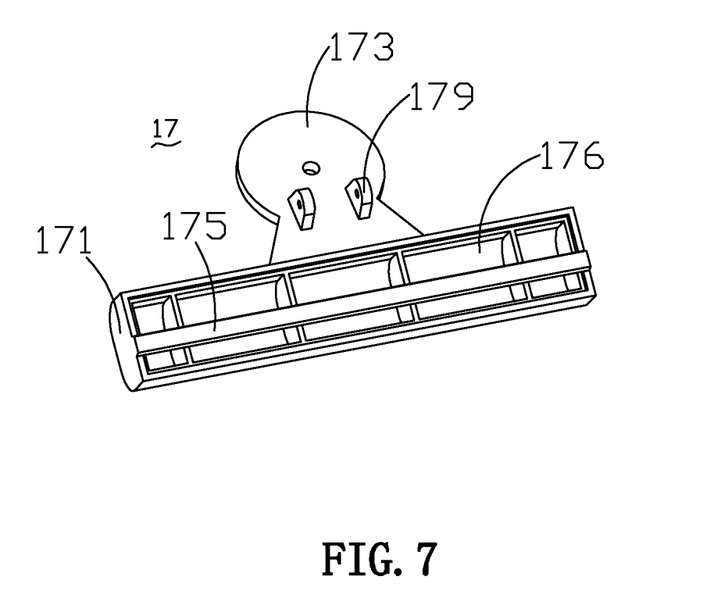
FIG. 7 is an enlarged view of the second holding body of FIG. 3.

Referring to FIG. 7, the second holding body 17 includes a clamping holder 171 and a second operation knob 173. The second operation knob 173 extends from the clamping holder 171. A clipping protrusion 175 extends from the clamping holder 171. The clamping holder 171 defines a number of cavities 176, for reducing weight thereof.

Referring to FIGS. 2 and 3 again, during assembly of the clamping member 1, the first operation knob 112 and the second operation knob 173 are pivotably mounted together. The clipping protrusion 175 is engaged in the through groove 156, to form the through hole 10 with the flutes 155 and the fixing groove 118. The first operation knob 112 and the second operation knob 173 are urged or released to move away or towards clip the perfusion tube into the through hole 10. Specifically, referring to FIGS. 4 and 7, two opposite tabs 123 extend from the first operation knob 112, and two opposite tabs 178 also extend from the second operation knob 173. Each tab 123 and 175 defines a pivot hole (not labeled). The clamping member 1 further includes two fixing shafts (not labeled). Each fixing shaft passes through the pivot holes of one tab 123 and the corresponding tab 175, to mount the first holding body 11 and the second holding body 17 together.

In the other embodiment, each of the first operation knob 112 and the second operation knob 173 only has one tab, and the clamping member 1 includes one fixing shaft. The clamping member 1 further includes a torsion spring (also not labeled), to conveniently restore the first holding body 11 and the second holding body 17. Therefore, the fixing shaft passes through the pivot holes of tabs, with the torsion spring sleeved onto the fixing shaft, and two feet of the torsion spring respectively against the first operation knob 112 and the second operation knob 173.

Referring to FIG. 1, the temperature-controlled unit 3 further includes chassis 37, with the adjusting current circuit 33 accommodating therein. Obviously, the adjusting current circuit 33 is integrated in a circuit board, and the circuit board is fitted in the chassis, together with the adjusting current circuit 33. The chassis 37 defines a wire hole (not labeled) and a mounting hole (not labeled). Two power wires 7 together pass through the wire hole and the fixing hole of the side panel 114 of the clamping member 1, to connect opposite ends of the heating member 31 and the adjusting current circuit 33, respectively. The heating member 31 is in series with the adjusting current circuit 33. The adjusting button 35 mounts in the mounting hole, also in series with the adjusting current circuit 33. In Detail, referring to FIG. 9, the adjusting current circuit 33 includes a slide rheostat 331. The slide rheostat 331 is in series with the heating member 31. The adjusting button 35 is movably mounted to the slide rheostat 331. The adjusting button 35 is slid along the slide rheostat 331 to change the resistance value of the adjusting current circuit 33, so that the current flows through the beating member 13 is changed. Therefore, heat of the heating member 31 becomes changed.

The power adapter 5 includes a transformer and a booster, used for adjusting power voltage to supply voltage. In this embodiment, the transformer and booster adjust the power voltage to 12V, which is the proper voltage for the temperature-controlled unit 3.

Figure 2:
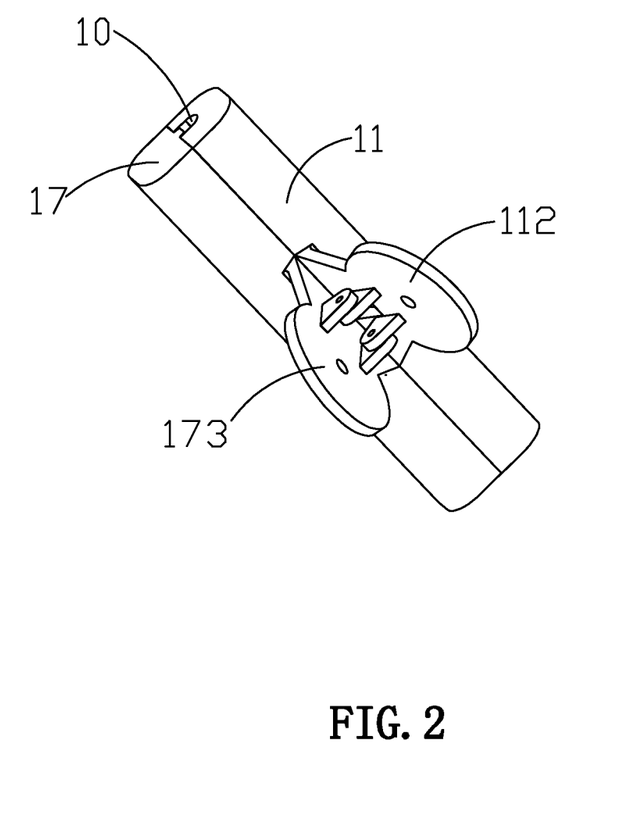
FIG. 2 is an assembled view of the clamping member of FIG. 1.
Figure 3:
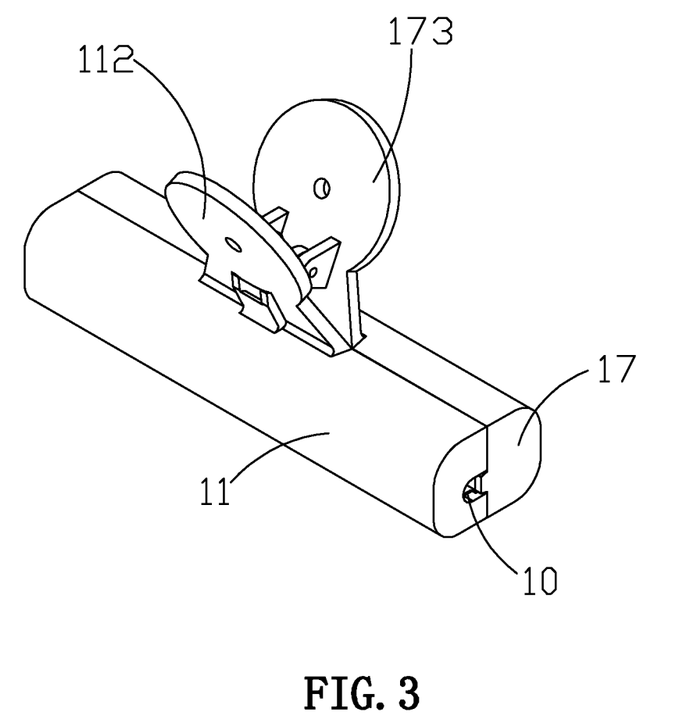
FIG. 3 is similar to FIG. 1, but viewed from another aspect; the clamping member comprising a first holding body, a second holding body, a securing member, and a cover plate.

Referring to FIGS. 1 to 3, by using the temperature-adjusted heater for transfusion, the power cord 51 is connected to the power supply, and then, the power adapter 5 provides a proper voltage for the temperature-controlled unit 3. Therefore, the adjusting current circuit 33 switches on, with the current flowing through the heating member 31 to generate heat. The first operation knob 112 and the second operation knob 173 are urged to move away to grasp the perfusion tube. When the perfusion tube is received into the through hole 10, the first operation knob 112 and the second operation knob 173 are released to move towards to fix the perfusion tube. Therefore, the perfusion tube is firmly against the heating member 31, and the transfusion liquid will become hot because of the heat of the heating member 31. According to requirement and feeling of the patient, the adjusting button 35 is conveniently operated to change the resistance value of the adjusting current circuit 33, so that the current flows through the beating member 13 is changed. Therefore, heat of the heating member 31 becomes changed and controlled, so that the temperature of the transfusion liquid substantially remains unchanged.

In the other embodiment, the clamping member 1 further includes a temperature sensor (not labeled) and a display (not labeled) electrically connected to the temperature sensor. The temperature sensor abuts against the transfusion tub, for detecting the temperature of the transfusion liquid flowing through the clamping member 1, which is shown in the display. Therefore, the patient or medical workers conveniently operate the adjusting button 35 according to the temperature shown in the display.

In the other embodiment, the chassis 37 and the adjusting current circuit 33 can be omitted, and the side panel 114 of the clamping member 1 defines an installing hole. The adjusting button 35 is mounted in the installing hole, and electrically connected to the heating member 31. Specifically, the adjusting button 35 is movably mounted to the heating member 31, and can be slid along the slide rheostat 331 to change the resistance value of the heating member 31. In this condition, the heating member 31, the adjusting button 35, and the power adapter 5 forms a circuit. The adjusting button 35 is slid to change the resistance value of the heating member 31, to change heat of the heating member 31. Therefore, the temperature of the transfusion liquid substantially can be adjusted.

Other applications, advantages, alternations, modifications, or equivalents to the disclosed embodiments are obvious to those skilled in the art.

What is claimed is:

1. A temperature-adjusted heater for transfusion, comprising a clamping member and a temperature-controlled unit:
   the clamping member defining a through hole, for a transfusion tube pass through and fixed therein;
   the temperature-controlled unit connecting to power supply; and the temperature-controlled unit comprising a heating member, an adjusting current circuit, and an adjusting button;
   wherein the heating member is mounted in the clamping member, in communication with the through hole, and firmly against the transfusion tube;
   the heating member and the adjusting button are in series with the adjusting current circuit, and the adjusting button is operated to change the resistance value of the adjusting current circuit,
   wherein the adjusting current circuit comprises a slide rheostat;
   the slide rheostat is in series with the heating member;
   the adjusting button is movably mounted to the slide rheostat, and slid along the slide rheostat;
   the clamping member comprises a first holding body and a second holding body pivotably mounted to the second holding body;
   the first holding body defines a installing groove and a through groove communicating with the installing groove;
   the second holding body comprises a clipping protrusion engaged in the through groove, to form the through hole with the installing groove;
   the heating member is mounted in first holding body, and facing the through hole,
   wherein the first holding body comprises a mounting base, a securing plate fixed in the mounting base, and a cover plate fixed to the mounting base;
   the mounting base comprises two opposite end panels, and each end panel defines a fixing groove;
   the securing plate defines a mounting groove aligned with the through groove, for fixing the heating member;
   the cover plate presses the securing plate, with opposite ends of the cover plate against the corresponding end panel;
   the through groove is located on the cover plate, and the cover plate defines two flutes in communication with the through groove;
   the flutes and the fixing grooves are cooperative to form the installing groove,
   the first holding body further comprises a plurality of supporting panels mounted in the mounting base;
   a wedge-shaped block extends from each supporting panel, and the securing plate comprises a first side and a second side opposite to the first side;
   the first side defines a plurality of clipping holes, engaged with the wedge-shaped blocks, correspondingly; and
   the second side abuts against the cover plate, and the mounting groove is located on the second side.

2. The temperature-adjusted heater according to claim 1, further comprises a power adapter and a plurality of power wires, wherein the power adapter comprises a power cord connecting to the power supply;
   the temperature-controlled unit further comprises a chassis and a circuit board mounted in the chassis, the adjusting current circuit is integrated in the circuit board;
   the chassis defines a mounting hole, the adjusting button is mounted in the mounts the mounting hole, the power adapter, and the circuit board are electrically connected in series via the power wires.

3. The temperature-adjusted heater according to claim 1, wherein a rib protrudes from the first side;
   each supporting panel defines a receiving groove aligned with each other to locked the rib.

4. The temperature-adjusted heater according to claim 1, wherein the cover plate comprises a plate and two connecting blocks;
   the through groove extends through the opposite ends of the plate to divide the plate into two sub-plates;
   the connecting blocks respectively connect to opposite ends of the plate, and each flute extends through the corresponding connecting block.

5. The temperature-adjusted heater according to claim 1, wherein the clamping member further comprises a temperature sensor and a display electrically connected to the temperature sensor;
   the temperature abuts against the transfusion tube, for detecting the temperature of the transfusion liquid flowing through the clamping member, which is shown in the display.

6. The temperature-adjusted heater according to claim 1, wherein further comprises a power adapter, wherein the power adapter comprises a power cord connecting to the power supply;
   the heating member, the adjusting button, and the power adapter forms a circuit.

* * * * *